(12) United States Patent
Cho

(10) Patent No.: US 7,488,216 B2
(45) Date of Patent: Feb. 10, 2009

(54) CONNECTOR TO RECEIVE BLOOD TEST CHIPS FOR USE WITH A BLOOD-SUBSTANCE MEASURING DEVICE

(75) Inventor: Ching Hsin Cho, Wugu Hsiang (TW)

(73) Assignee: Biomedix Taiwan Co., Ltd., Wugu Hsiang, Taipei Hsien (TW)

( * ) Notice: Subject to any disclaimer, the term of this patent is extended or adjusted under 35 U.S.C. 154(b) by 530 days.

(21) Appl. No.: 11/292,700

(22) Filed: Dec. 2, 2005

(65) Prior Publication Data

US 2007/0128074 A1    Jun. 7, 2007

(51) Int. Cl.
*H01R 25/00* (2006.01)
(52) U.S. Cl. ........................ 439/638; 439/909
(58) Field of Classification Search ............... 439/638, 439/909
See application file for complete search history.

(56) References Cited

U.S. PATENT DOCUMENTS

| | | | | |
|---|---|---|---|---|
| 6,733,328 B2* | 5/2004 | Lin et al. | | 439/501 |
| 6,751,694 B2* | 6/2004 | Liu et al. | | 710/301 |
| 2003/0211784 A1* | 11/2003 | Wu et al. | | 439/638 |
| 2006/0258224 A1* | 11/2006 | Liao | | 439/638 |
| 2007/0068808 A1* | 3/2007 | Lee | | 204/403.01 |

* cited by examiner

*Primary Examiner*—Tho D Ta
(74) *Attorney, Agent, or Firm*—patenttm.us

(57) ABSTRACT

A connector to receive blood test chips for use with a blood-substance measuring device includes a receptacle, a plug and a wire lead. The receptacle has two ends and a slot. The slot is formed on one end of the receptacle and receives a test chip. The wire lead connects to the other end of the receptacle and the plug. The plug is adapted to be inserted into a corresponding socket in the blood-substance measuring device to electrically connect the test chip to the device.

3 Claims, 6 Drawing Sheets

CONNECTOR TO RECEIVE BLOOD TEST CHIPS FOR USE WITH A BLOOD-SUBSTANCE MEASURING DEVICE

BACKGROUND OF THE INVENTION

1. Field of the Invention

The present invention relates to a connector to receive blood test chips, and especially a connector to receive blood test chips to be used with a blood-substance measuring device having a connector.

2. Description of the Related Art

With the development of medical science, medical devices for use at home have improved. A convenient blood testing device that can provide immediate test results is important to some patients, such as diabetics.

A conventional blood testing device has a body and a slot. The slot receives a blood test chip and is formed in the body. When a user uses the device to analyze a blood sample for a substance level, such as blood-glucose, the user drops a small amount of blood from a finger onto a blood test chip. The sample reacts with a reaction film on the blood test chip. The user then inserts the blood test chip into the slot of the device to get a reading of the blood-substance level.

However, the size of the blood-substance measuring device and the location of the slot can make the device difficult or awkward for some people to use, such as arthritis sufferers or the elderly.

SUMMARY OF THE INVENTION

The objective of the present invention is to provide a connector to receive blood test chips that can be used with a blood-substance measuring device and allows a user to conveniently and easily use the blood-substance measuring device.

In order to achieve the above objective, the connector to receive blood test chips for use with a blood-substance measuring device includes a receptacle, a plug and a wire lead. The receptacle has two ends and a slot. The slot is formed on one end of the receptacle and receives a test chip. The wire lead is connected to the other end of the receptacle and the plug. The plug connects to a socket of a blood-substance measuring device.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
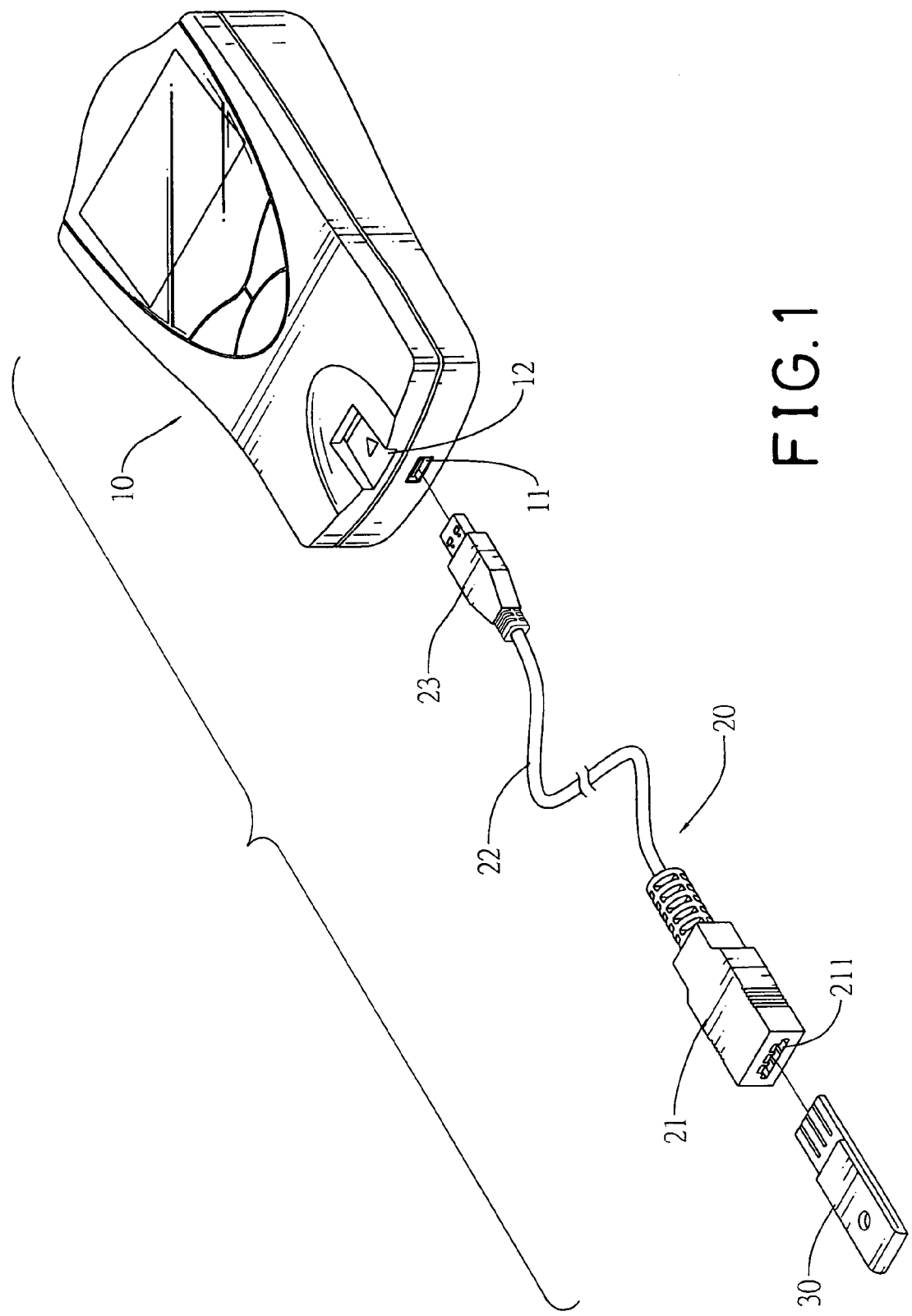
FIG. 1 is a partially exploded operational perspective view of a first embodiment of a connector of the present invention.

With reference to FIG. 1, a first embodiment of a connector (20) to receive blood test chips in accordance with the present invention is used with a blood-substance measuring device (10).

The blood-substance measuring device (10) has a body, a processor, relevant circuitry, a socket (11) and a slot (12). The processor is mounted in the body to determine the concentration of the blood substance. The relevant circuitry is also mounted in the body. The socket (11) and the slot (12) are formed respectively on the body and are connected to the relevant circuitry. The slot (12) can receive a test chip (30) to detect the concentration of the blood substance.

The connector (20) has a receptacle (21), a wire lead (22) and a plug (23). The receptacle (21) has two ends and a slot (211). The slot (211) is formed in one end of the receptacle (21) and receives a test chip (30) with a blood sample. An end of the wire lead (22) is connected to the other end of the receptacle (21). The other end of the wire lead (22) is connected to the plug (23). The plug (23) is connected to a corresponding socket (11) in the blood-substance measuring device (10). The plug (23) is a universal serial bus (USB) in the first embodiment and the socket (11) is a corresponding USB socket.

Figure 2:
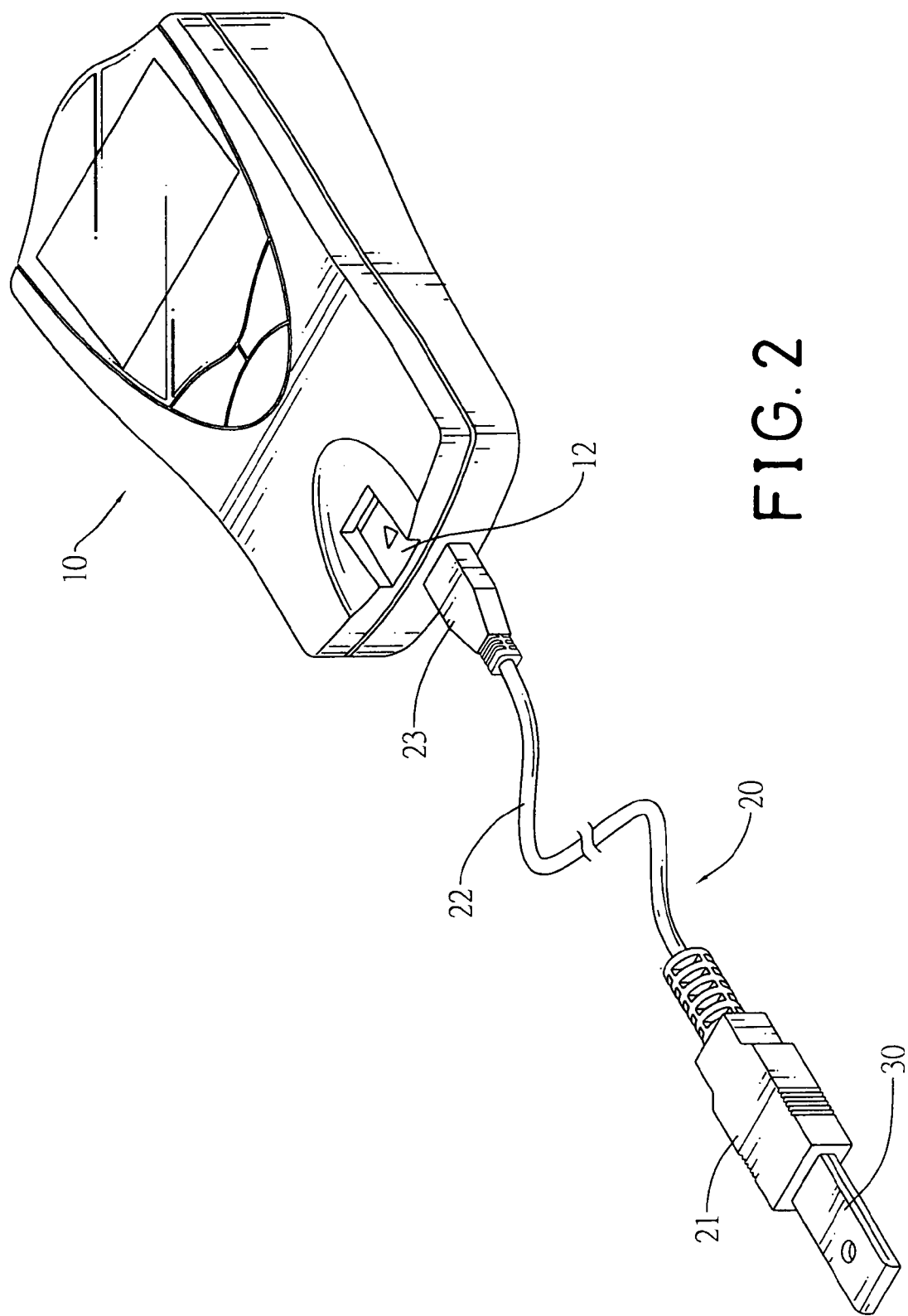
FIG. 2 is an operational perspective view of the first embodiment of the connector in FIG. 1.

With reference to FIG. 2, a reaction film is formed on the test chip (30) to test for a particular substance in the blood. The test chip (30) is received into the slot (211) on the receptacle (21) of the connector (20). The test chip (30) can then be touched to a user's blood on the skin or the blood can be dripped onto the test chip (30). The blood sample reacts with the reaction film. In several seconds, the blood-substance measuring device (10) provides a current to the slot (211) via the wire lead (22). Then the current goes through the reaction film to complete a circuit so that the concentration of the particular substance in the blood is determined and displayed by the blood-substance measuring device (10).

The invention eliminates the need for a user to insert the test chip (30) into the slot (12) on the blood-substance measuring device (10), although the slot (12) is still fully functional. The small receptacle (21) of the connector (20) is easier to handle than the body of the measuring device (10). The length of the wire lead (22) can also be varied.

Figure 3:
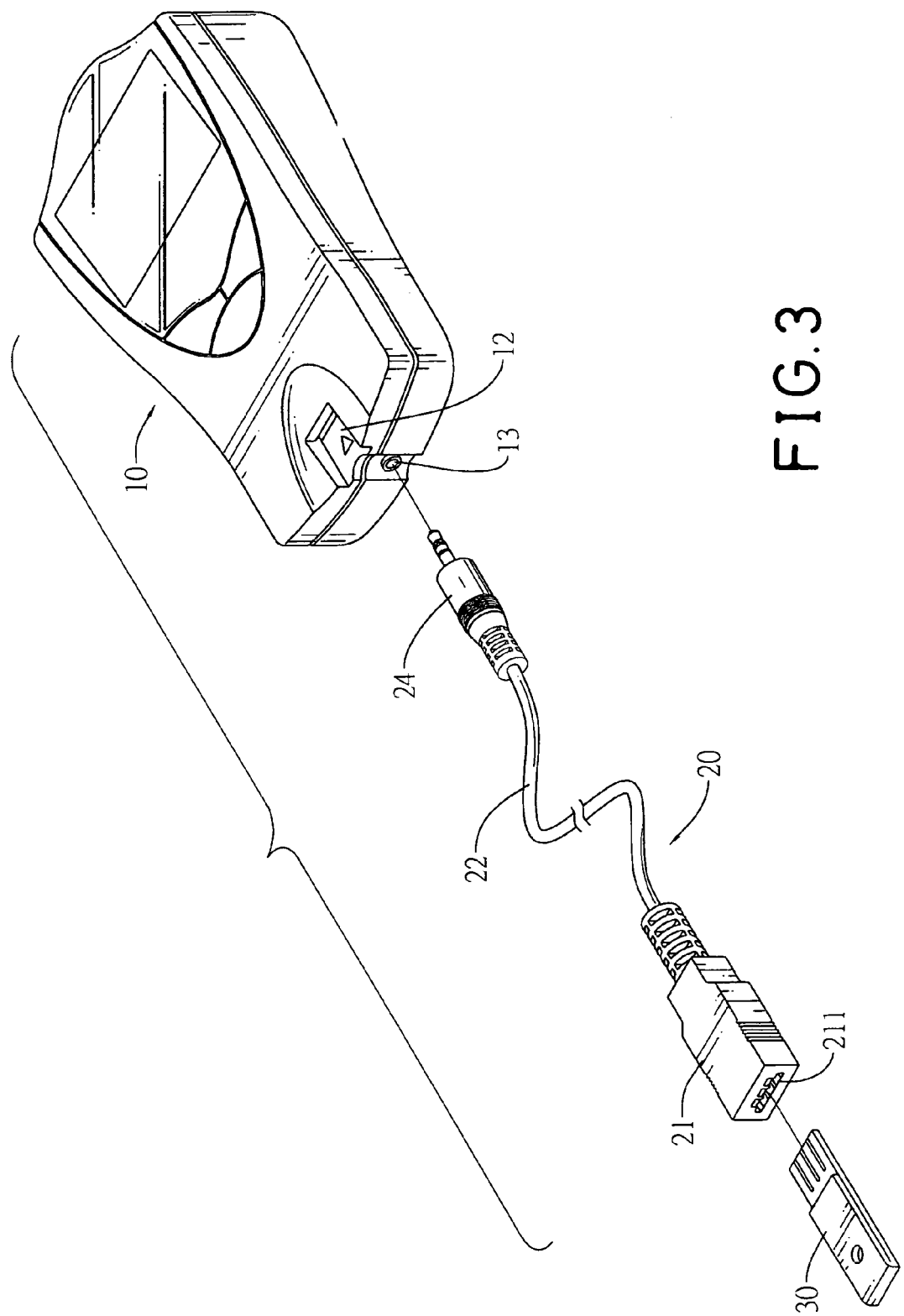
FIG. 3 is a partially exploded operational perspective view of a second embodiment of a connector of the present invention.
Figure 4:
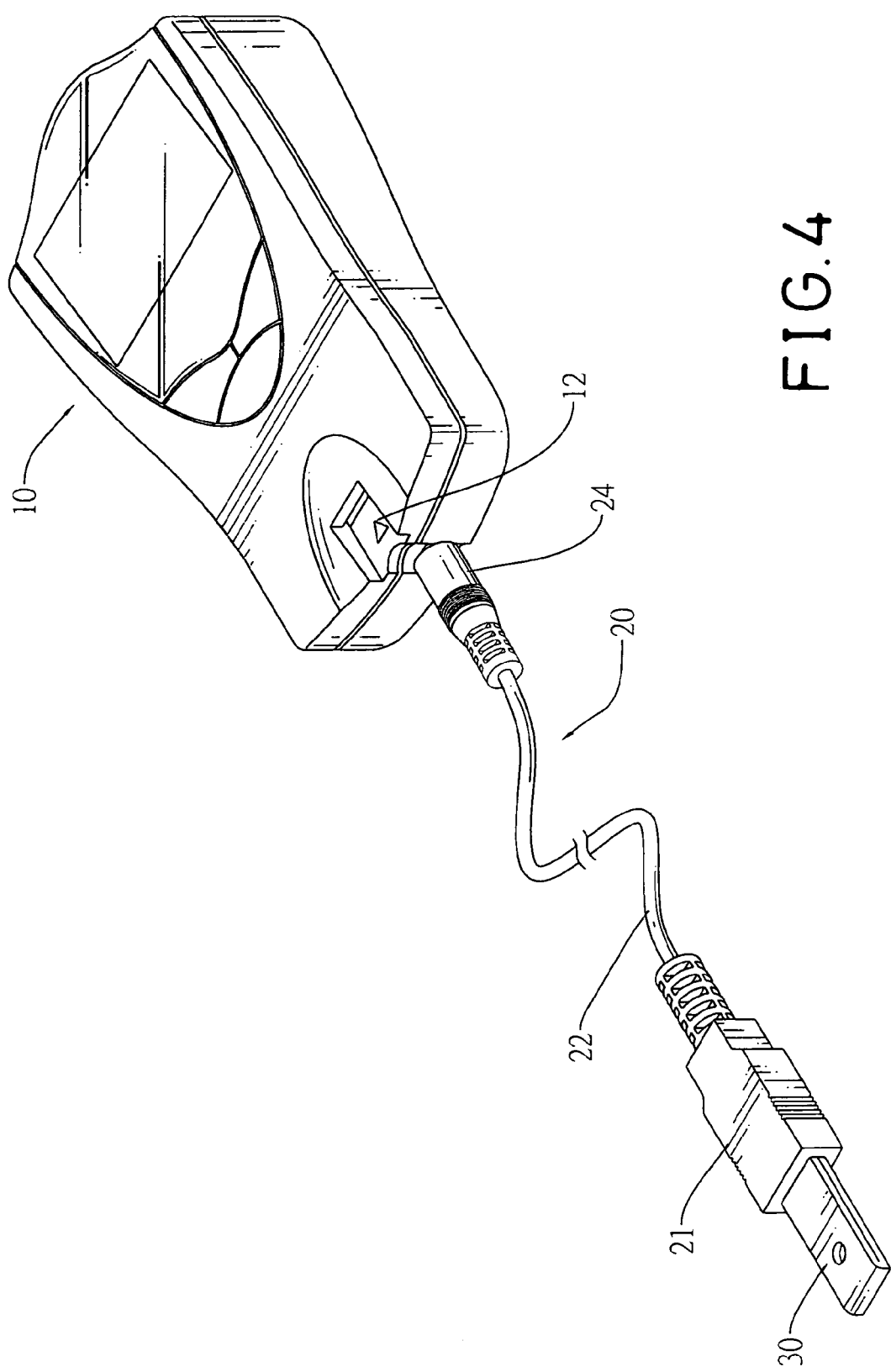
FIG. 4 is an operational perspective view of the second embodiment of the connector in FIG. 3.

With reference to FIGS. 3 and 4, in a second embodiment of a connector to receive blood test chips for use with a blood-substance measuring device in accordance with the present invention, the connector (20) is similar to the connector (20) in the first embodiment. However, a regular audio-type jack is used as a plug (24) in the second embodiment, which is different from the plug (23) used in the first embodiment. The plug (24) is inserted into a corresponding socket (13) in the blood-substance measuring device (10).

Figure 5:
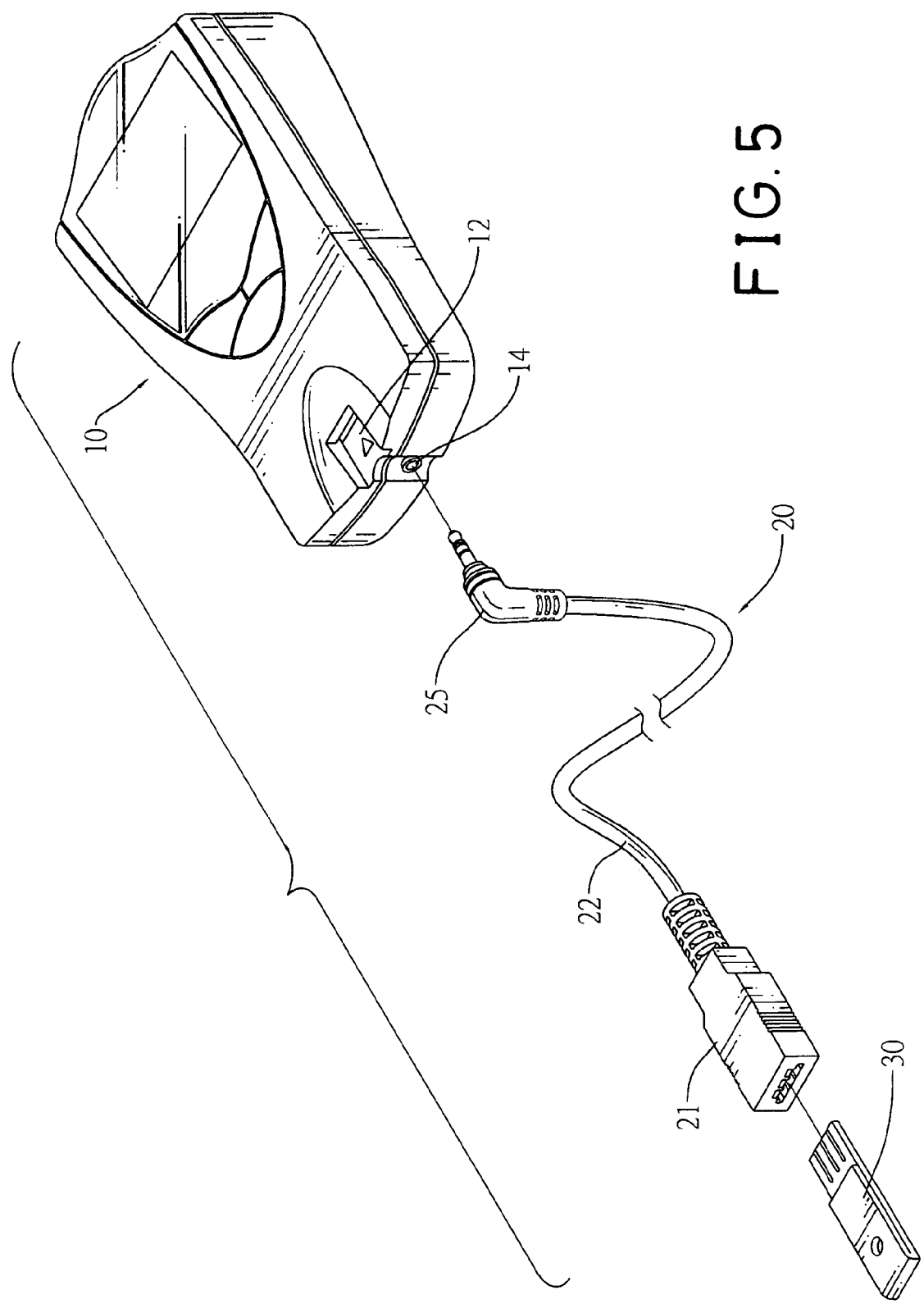
FIG. 5 is a partially exploded operational perspective view of a third embodiment of a connector of the present invention.
Figure 6:
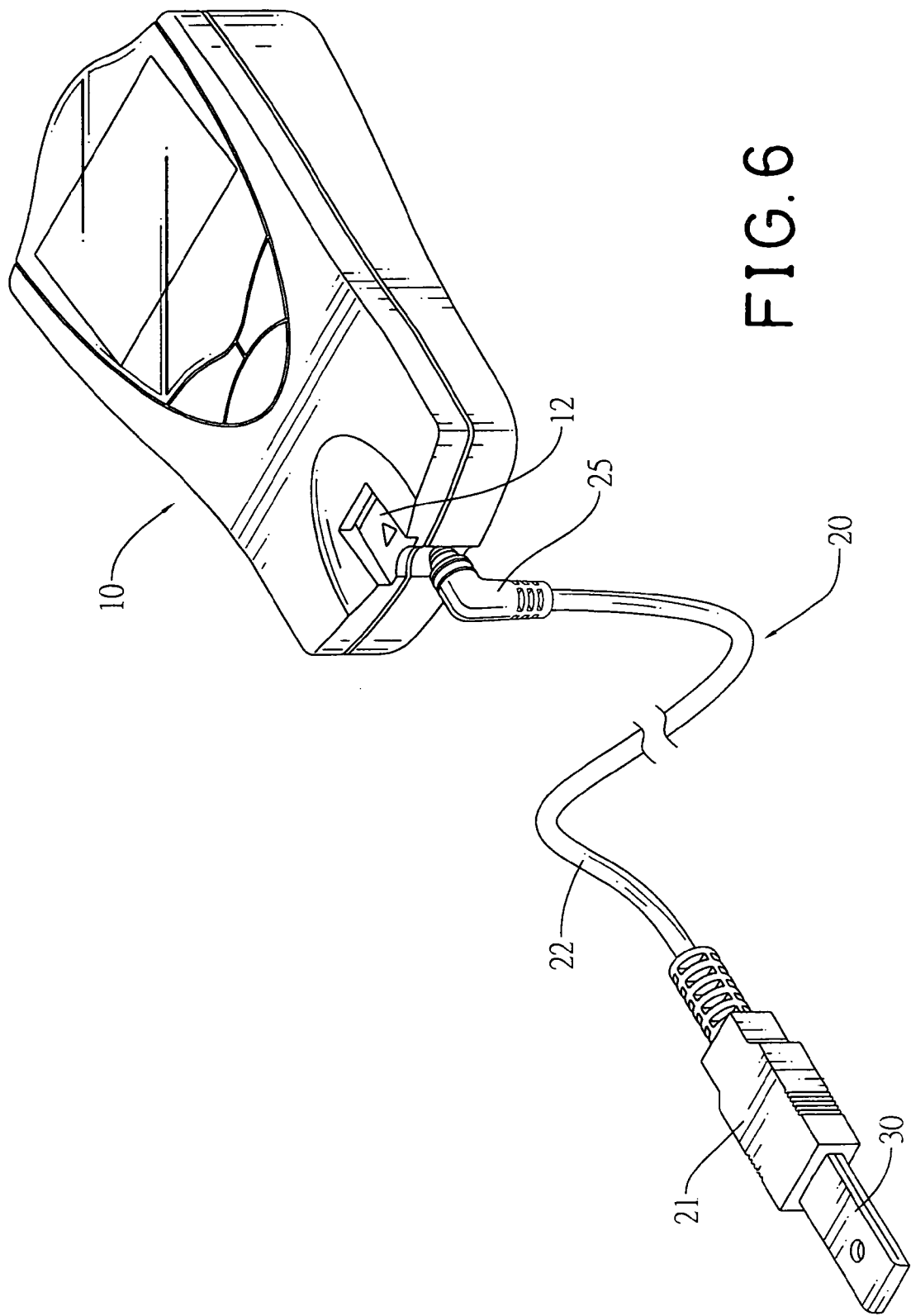
FIG. 6 is an operational perspective view of the third embodiment of the connector in FIG. 5.

With reference to FIGS. 5 and 6, in a third embodiment of the connector to receive blood test chips for use with a blood-substance measuring device in accordance with the present invention, the connector (20) is similar to the connector in the second embodiment. An audio-type jack with a 90-degree angle is used as a plug (25) in the third embodiment and is inserted in a corresponding socket (14).

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A blood-substance measuring device comprising:
   a body;
   a processor being mounted in the body to determine concentration of a blood substance;
   relevant circuitry being mounted in the body;
   a socket being formed on the body and being connected to the relevant circuitry; and
   a slot being formed on the body and being connected to the relevant circuitry for receiving a test chip to detect the concentration of the blood substance; and
   a connector including
      a receptacle having
         two ends, and
         a slot formed on one end of the receptacle to receive a test chip;
      a plug being adapted to be inserted into the socket; and
      a wire lead with two ends, one end connecting to the other end of the receptacle and an opposite end connecting to the plug.

2. The blood-substance measuring device of the claim 1, wherein the plug is a universal serial bus (USB) type plug.

3. The blood-substance measuring device of the claim 1, wherein the plug is an audio-type jack.

* * * * *